(12) United States Patent
Van Der Schaaf et al.

(10) Patent No.: US 7,432,380 B2
(45) Date of Patent: Oct. 7, 2008

(54) CRYSTALLINE FORM OF FLUVASTATIN SODIUM

(75) Inventors: Paul Adriaan Van Der Schaaf, Hagenthal-le-Haut (FR); Fritz Blatter, Reinach (CH); Martin Szelagiewicz, Münchenstein (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 10/576,784

(22) PCT Filed: Oct. 6, 2004

(86) PCT No.: PCT/EP2004/052449

§ 371 (c)(1),
(2), (4) Date: Apr. 21, 2006

(87) PCT Pub. No.: WO2005/037787

PCT Pub. Date: Apr. 28, 2005

(65) Prior Publication Data

US 2006/0241167 A1    Oct. 26, 2006

(30) Foreign Application Priority Data

Oct. 16, 2003  (EP) .................. 03103841

(51) Int. Cl.
*C07D 209/12*  (2006.01)
(52) U.S. Cl. .................. 548/494
(58) Field of Classification Search ........ 548/494; 514/419
See application file for complete search history.

(56) References Cited

U.S. PATENT DOCUMENTS

| | | | |
|---|---|---|---|
| 4,739,073 A | 4/1988 | Kathawala | 548/406 |
| 6,124,340 A | 9/2000 | Horvath | 514/419 |
| 6,696,479 B2 * | 2/2004 | Van Der Schaaf et al. | 514/410 |
| 6,743,926 B2 | 6/2004 | Wolleb et al. | 548/494 |
| 6,858,643 B2 * | 2/2005 | Van Der Schaaf et al. | 514/419 |
| 2003/0032666 A1 | 2/2003 | Van Der Schaaf et al. | 514/419 |
| 2003/0125569 A1 | 7/2003 | Van Der Schaaf et al. | 548/494 |
| 2005/0032875 A1 | 2/2005 | Wolleb et al. | 514/419 |
| 2005/0038114 A1 | 2/2005 | Lifshitz-Liron et al. | 514/548 |
| 2006/0105441 A1 | 5/2006 | Ohrlein et al. | 435/136 |

FOREIGN PATENT DOCUMENTS

| | | |
|---|---|---|
| WO | 97/49681 | 12/1997 |
| WO | 02/36563 | 5/2002 |
| WO | 03/013512 | 2/2003 |
| WO | 2004/096765 | 11/2004 |
| WO | 2004/113291 | 12/2004 |
| WO | 2004/113292 | 12/2004 |

OTHER PUBLICATIONS

Polymorphism in Pharmaceutical Solids, edited by Brittain, 1999, Marcel Dekker Inc., p. 1-2, 178-179, 185, 219 and 236.*
U.S. Pharmacopia #23, National Formulary #18 (1995), p. 1843-1844.*
Bernstein, "Polymorphism in molecular crystals," 2002, p. 117-118 and 272.*
Davidovich et al., "Detection of polymorphism . . . " Am. Pharm. Rev. vol. 7(1), 2004, p. 10, 12, 14, 16, 100.*
A. Maureen Rouhi, Chemical & Enginnering News, Feb. 24, 2004, p. 32-35.*
Haleblian et al. Journal of Pharmaceutical Science, Aug. 1969, vol. 58, No. 8, p. 911-929.*

* cited by examiner

*Primary Examiner*—Rei-Tsang Shiao
(74) *Attorney, Agent, or Firm*—Mervin G. Wood

(57) ABSTRACT

A novel crystalline form of Fluvastatin sodium hydrate is described, referred to hereinafter as polymorphic Form G. Furthermore, processes for the preparation of this crystalline form and pharmaceutical compositions comprising this crystalline form are reported.

8 Claims, 1 Drawing Sheet

CRYSTALLINE FORM OF FLUVASTATIN SODIUM

This application is a 371 of PCT/EP04/52449 filed on Oct. 6, 2004.

The present invention is directed to novel crystalline form of Fluvastatin sodium, processes for the preparation and pharmaceutical compositions comprising this crystalline form.

Fluvastatin sodium is known by its chemical name (±)-7-(3-(4-fluorophenyl)1-1-methylethyl)-1H-indol-2-yl)-3,5-dihydroxy-6-heptenoic acid monosodium salt. Fluvastatin sodium is a racemic mixture of the 3R,5S- and 3S,5R-dihydroxy enantiomers and has the following formula:

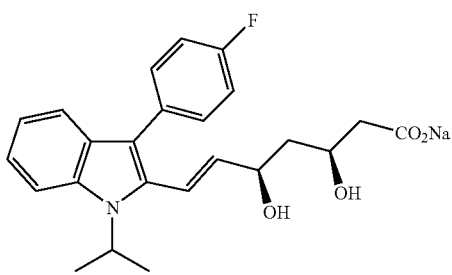

Fluvastatin sodium is an inhibitor of 3-hydroxy-3-methylglutaryl coenzyme A (HMG-CoA) and is used to lower the blood cholesterol level.

Fluvastatin sodium salt is disclosed in U.S. Pat. No. 4,739,073. In this patent Fluvastatin sodium is obtained by lyophilization. WO-A-97/49681 and its US equivalent U.S. Pat. No. 6,124,340 describe that lyophilization of Fluvastatin sodium yields a mixture of a crystalline form, designated as Form A, and amorphous material, and disclose a new crystalline form, designated as Form B. WO-A-03/13512 discloses 4 new crystalline hydrates, designated as Forms C, D, E and F. These crystalline hydrates have water contents which ranges from 3 to 32%. The stability of these new crystalline hydrates very much depend on the relative air humidity of the surrounding atmosphere. For example, Form D is the most stable crystalline form in atmospheres with an air humidity ranging from 30 to 50%, whereas Form F is stable in atmospheres with an air humidity of up to 90%. However, there is still a need for stable crystalline forms which can be used for example in gel or wet formulations.

It has now been found that Fluvastatin sodium can surprisingly be prepared as a novel crystalline hydrate, which is stable in saturated aqueous environments. This novel crystalline hydrate, herein designated as Form G, is a liquid crystalline material which, for example, allows gel or wet formulations of Fluvastatin sodium.

U.S. Pat. No. 6,696,479 discloses novel crystalline forms of fluvastatin sodium hydrates.

U.S. Pat. No. 6,858,643 discloses crystalline forms of the (3R,5S) and the (3S5R) enantiomers of fluvastatin.

Thus the present invention provides the following novel crystalline form of Fluvastatin sodium:

A crystalline polymorph of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å): 29.2 (w), 15.0 (vw), 10.1 (m), 7.6 (vs), 6.10 (s), 5.09 (m), 4.37 (s), 3.83 (w), 3.07 (m), herein designated as Form G. The abbreviations in brackets mean: (vs)=very strong intensity; (s)=strong intensity; (m)=medium intensity; (w)=weak intensity; and (vw)=very weak intensity. A characterisitic X-ray powder diffraction pattern for Form G is depicted in FIG. 1.

Furthermore, the present invention is directed to processes for the preparation of Form G. Form G of Fluvastatin sodium can generally be prepared from any crystalline Form or amorphous Fluvastatin sodium, or mixtures thereof, for example, by filtration of an aqueous suspension. The suspension may be obtained, for example, by introducing amorphous or any crystalline form of Fluvastatin sodium, e.g. form A, B, C, D, E or F, into water, usually, the amount of water used is insufficient to dissolve significant amounts of the material, e.g. by using the about 2-10 fold weight of water, relative to Fluvastatin sodium. It may also be obtained by crystallizing or partially crystallizing Fluvastatin sodium in water, e.g. by cooling of a solution or diluted suspension in water.

As a rule, the water content in the present Form G is 30% by weight or more. Small changes in the water content can cause small deviations in the d-values of characteritic peaks in the X-ray powder diffraction patterns.

Another object of the present invention are pharmaceutical compositions comprising an effective amount of crystalline polymorphic Form G, and a pharmaceutically acceptable carrier. The polymorphic form G may be used as a single component or as a mixture with other crystalline forms or the amorphous form of Fluvastatin sodium.

As to pharmaceutical compositions of Fluvastatin sodium it is preferred that these contain 25-100% by weight, especially 50-100% by weight, of Form G, based on the total amount of Fluvastatin sodium. Preferably, such an amount of Form G of Fluvastatin sodium is 75-100% by weight, especially 90-100% by weight. Highly preferred is an amount of 95-100% by weight.

The compositions of the invention include powders, granulates, aggregates and other solid compositions comprising crystalline polymorphic form G. In addition, the compositions that are contemplated by the present invention may further include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl, cellulose salts and other substituted and unsubstituted celluloses; starch; pregelatinized starch; inorganic diluents like calcium carbonate and calcium diphosphate and other diluents known to the pharmaceutical industry. Yet other suitable diluents include waxes, sugars and sugar alcohols like mannitol and sorbitol, acrylate polymers and copolymers, as well as pectin, dextrin and gelatin. Of special importance are aqueous gels or liquid formulations.

Further excipients that are within the contemplation of the present invention include binders, such as acacia gum, pregelatinized starch, sodium alginate, glucose and other binders used in wet and dry granulation and direct compression tableting processes. Excipients that also may be present in the solid compositions further include disintegrants like sodium starch glycolate, crospovidone, low-substituted hydroxypropyl cellulose and others. In addition, excipients may include tableting lubricants like magnesium and calcium stearate and sodium stearyl fumarate; flavorings; sweeteners; preservatives; pharmaceutically acceptable dyes and glidants such as silicon dioxide.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of Fluvastatin sodium whereupon the properties that distinguish the solid forms of Fluvastatin sodium are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Preferred unit dosages of the pharmaceutical compositions of this invention typically contain from 0.5 to 100 mg of the novel Fluvastatin sodium form or mixtures thereof with each other or other forms of Fluvastatin sodium. More usually, the combined weight of the Fluvastatin sodium forms of a unit dosage are from 2.5 mg to 80 mg, for example 5, 10, 20 or 40 mg.

The following Examples illustrate the invention in more detail. Temperatures are given in degrees Celsius. All percentages are given by weight if not otherwise indicated.

EXAMPLE 1

Preparation of Polymorphic Form G 300 mg of Fluvastatin sodium Form A are suspended in 1.0 ml water at ambient temperature. The resulting suspension is stirred for 18 hours. The solid residue is separated by filtration. Without any further drying, the obtained solid paste is investigated by powder X-ray diffraction in a dosed sample chamber under an adjusted relative humidity of about 90% or higher. The X-ray powder diffraction pattern is depicted in FIG. 1.

Exactly the same result is obtained when example 1 is repeated and the solid residue is filtered after only 15 minutes of stirring.

Also the same results are obtained when example 1 is repeated starting from any other crystalline form of Fluvastatin sodium.

Figure 1:
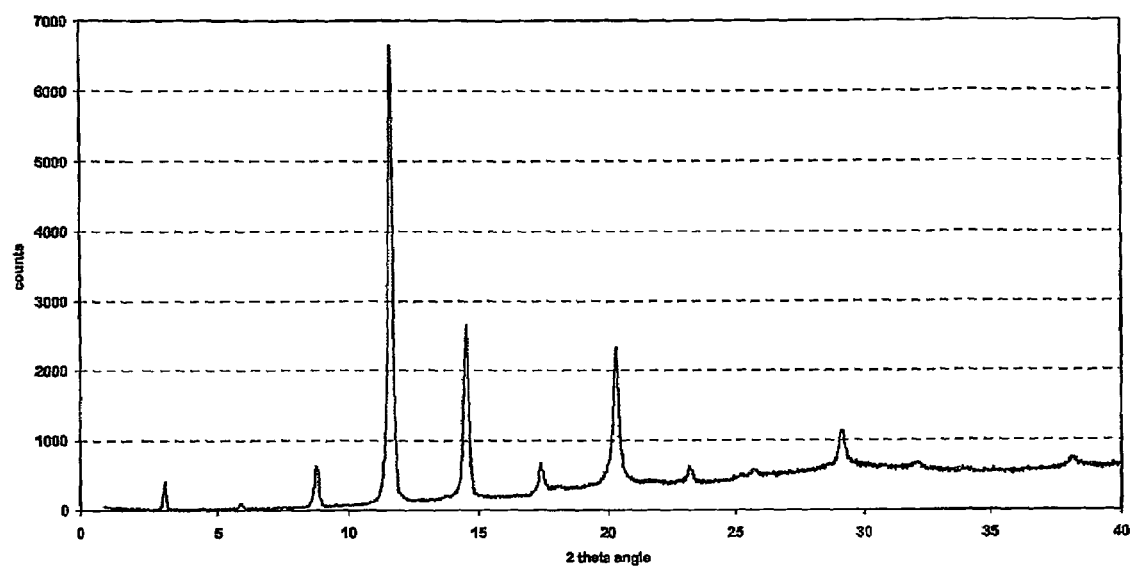
FIG. 1 is a characteristic X-ray powder diffraction pattern for Form G.

The invention claimed is:

1. A crystalline polymorph Form G of (±)-7-(3-(4-fluorophenyl)-1-(1-methylethyl)-1H-indol-2-yl)-3,5-dihydroxy-6-heptenoic acid monosodium salt which exhibits a characteristic X-ray powder diffraction pattern with characteristic peaks expressed in d-values (Å): 29.2 (w), 15.0 (vw), 10.1 (m), 7.6 (vs), 6.10 (s), 5.09(m), 4.37 (s), 3.83 (w) and 3.07(m), wherein (vs)=very strong intensity, (s)=strong intensity, (m)=medium intensity, (w)=weak intensity and (vw)=very weak intensity.

2. A crystalline polymorph Form G of (±)-7-(3-(4-fluorophenyl)-1-(1-methylethyl)-1H-indol-2-yl)-3,5-dihydroxy-6-heptenoic acid monosodium salt according to claim 1 which exhibits a characteristic X-ray powder diffraction pattern with characteristic peaks expressed in d-values (Å): 7.6 (vs), 6.10 (s), and 4.37 (s), wherein (vs)=very strong intensity and (s)=strong intensity.

3. A crystalline polymorph Form G of (±)-7-(3-(4-fluorophenyl)-1-(1-methylethyl)-1H-indol-2-yl)-3,5-dihydroxy-6-heptenoic acid monosodium salt according to claim 1 which exhibits a characteristic X-ray powder diffraction pattern with characteristic peaks expressed in d-values (Å): 10.1 (m), 7.6 (vs), 6.10 (s), 5.09 (m), 4.37 (s) and 3.07 (m), wherein (vs)=very strong intensity, (s)=strong intensity and (m)=medium intensity.

4. A process for the preparation of crystalline polymorph Form G according to claim 1, wherein Fluvastatin sodium is filtered off from an aqueous suspension.

5. A process according to claim 4 for in which the aqueous suspension is prepared from any of the known crystalline forms or the amorphous form of Fluvastatin sodium.

6. A process according to claim 4 in which an aqueous suspension of Fluvastatin sodium is stirred before filtration.

7. A process for the preparation of crystalline polymorph Form G according to claim 3, wherein Fluvastatin sodium is filtered off from an aqueous suspension.

8. A process for the preparation of crystalline polymorph Form G according to claim 2, wherein Fluvastatin sodium is filtered off from an aqueous suspension.

* * * * *